(12) United States Patent
Phillips et al.

(10) Patent No.: US 10,617,857 B1
(45) Date of Patent: Apr. 14, 2020

(54) RASTER INJECTOR FOR MICROPIGMENTATION AND METHOD OF USE THEREOF

(71) Applicant: Spectra Tattooing Technologies LLC, Tulsa, OK (US)

(72) Inventors: Lisa L. Phillips, Tulsa, OK (US); Drew T. Morgan, Tulsa, OK (US)

(73) Assignee: Odd Pixel Tattooing Technologies, Inc., Tulsa, OK (US)

( * ) Notice: Subject to any disclaimer, the term of this patent is extended or adjusted under 35 U.S.C. 154(b) by 206 days.

(21) Appl. No.: 15/821,414

(22) Filed: Nov. 22, 2017

Related U.S. Application Data

(60) Provisional application No. 62/425,101, filed on Nov. 22, 2016.

(51) Int. Cl.
*A61M 37/00* (2006.01)
(52) U.S. Cl.
CPC .............................. *A61M 37/0084* (2013.01)
(58) Field of Classification Search
CPC .......... A61M 37/0084; A61M 37/0076; A01K 11/00; A61B 2090/395
USPC .......................................... 81/9.22; 606/186
See application file for complete search history.

(56) References Cited

U.S. PATENT DOCUMENTS

| | | | | |
|---|---|---|---|---|
| 2008/0247637 | A1* | 10/2008 | Gildenberg | A61B 18/203 382/153 |
| 2015/0359559 | A1* | 12/2015 | Scherkowski | A61B 17/32093 606/186 |

FOREIGN PATENT DOCUMENTS

| | | | | |
|---|---|---|---|---|
| NL | 8701696 | A * | 2/1989 | A01K 11/005 |

* cited by examiner

*Primary Examiner* — George J Ulsh
(74) *Attorney, Agent, or Firm* — Crowe & Dunlevy, P.C.

(57) ABSTRACT

The invention generally relates to a raster injector for micropigmentation and use thereof, and more particularly to a raster injector that precisely inserts pigment, medicine or other fluids into skin or other industrial materials. The raster injector is connected to a motion platform that enables the injector to inject pigment or other fluids into the layers of the skin or other substrates through micro, hollow point needles. The raster injector includes a disposable, interchangeable ink delivery assembly, an ink reservoir assembly and a non-disposable base assembly.

11 Claims, 6 Drawing Sheets

RASTER INJECTOR FOR MICROPIGMENTATION AND METHOD OF USE THEREOF

CROSS REFERENCE TO RELATED APPLICATIONS

The application claims the benefit of and priority to U.S. Provisional Patent Application No. 62/425,101, filed Nov. 22, 2016, and incorporates by reference said provisional application in its entirety.

BACKGROUND OF THE INVENTION

Field of the Invention

This invention relates generally to a raster injector for micropigmentation and use thereof, and more particularly to a raster injector that precisely inserts pigment, medicine or other fluids into skin or other industrial materials.

2. DESCRIPTION OF THE RELATED ART

Traditionally, micropigmentation (tattooing) is achieved by pushing pigment through the epidermis into the dermis with a small hand-held puncturing device, either manual or motorized, to achieve an indelible mark. Around the industrial revolution, Samuel O'Reilly patented the first Electric Tattoo Machine in 1891, modified from Edison's Autographic Engraving Pen patented in 1876. Throughout the years, although additional patents have been issued, very few significant changes have been made. In essence, all these devises are small, handheld, motors, either of the rotatory or electromagnetic coil variety.

Traditionally, colors are applied one at a time and the area is repeatedly gone over, causing severe pain. These traditional tattoo procedures can take many hours to complete and all the while, may suffer from errors of the human hand. By digitizing the entire process, a multitude of pain points will be resolved.

It is therefore desirable to provide a raster injector for micropigmentation and use thereof.

It is further desirable to provide a raster injector that precisely inserts pigment, medicine or other fluids into skin or other industrial materials.

It is still further desirable to provide a raster injector connected to a motion platform that enables the injector to inject pigment or other fluids into the layers of the skin or other materials through micro, hollow point needles.

It is yet further desirable to provide a raster injector for micropigmentation, which when used for tattooing, allows for greater detail with less trauma to the skin and produces higher quality tattoo designs with less pain, in a greatly decreased time frame. Further regarding the invention's use for tattooing, by using rows of hollow point needles that inject ink precisely where intended and where all colors are administered simultaneously in overlapping rows, the raster injector for micropigmentation provides more precision and detail to the designs, less trauma and less pain.

It is still yet further desirable to provide a raster injector for micropigmentation that may be used by dermatologists for a variety of procedures, such as correction of skin pigmentation issues, such as vitiligo, by color matching the patient's skin color and precisely printing the correct tone in the affected areas, by printing photo realistic aureoles of patients who have undergone a mastectomy or by treating severe varicose veins or scar tissue and stretch marks.

It is still yet further desirable to provide a raster injector for micropigmentation that may be used to inject pigments into foam or soft polymers, for the purpose of more durable graphics on specific products susceptible to paint loss or sun bleaching.

Other advantages and features will be apparent from the following description, and from the claims.

SUMMARY OF THE INVENTION

In general, the invention relates to a raster injector assembly for micropigmentation having a disposable, interchangeable ink delivery assembly with an array of needles. An ink reservoir assembly is configured to contain a plurality of inks and is in fluid communication with the ink delivery system. The raster injector assembly also includes a non-disposable base assembly connected to the ink delivery system the said ink reservoir assembly.

The array of needles may include biasing mechanisms, such as return springs. The ink delivery assembly includes a needle guide plate having axial bores that constrain motion of the needles in an axial direction. The ink delivery assembly may also include an ink distribution plate having one or more axial bore passageways and an array of induction chambers. A drive pin guide plate constrains motion of an array of drive pins in an axial direction. In addition, an array of drive grippers can engage a drive plate and/or said drive pin guide plate, with each of the drive grippers being respectively engaged with a drive pin.

Further, the ink reservoir assembly can include a plurality of ink reservoirs respectively containing inks. An ink pressure management system controls the flow of ink through the raster injector assembly.

Moreover, the base assembly of the raster injector assembly includes a motion platform configured to move the raster injector assembly in one or more directions. A drive mechanism of the motion platform provides a reciprocating, forced, relative motion between the base assembly and a drive plate of the raster injector assembly.

DETAILED DESCRIPTION OF THE INVENTION

Figure 1:
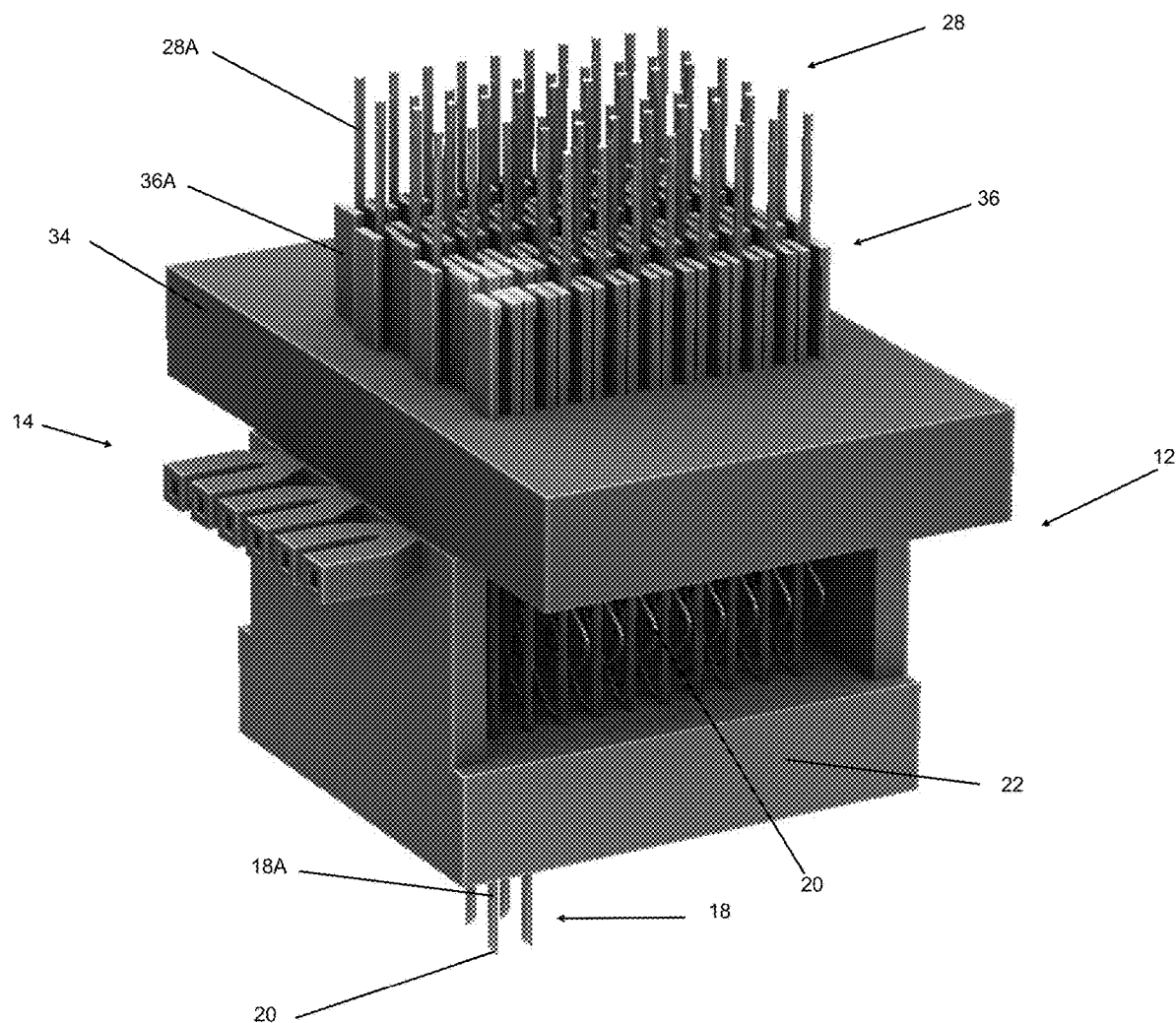
FIG. 1 is a perspective view of an example of a disposable, interchangeable ink deliver assembly in accordance with an illustrative embodiment of the raster injector disclosed herein.
Figure 2:
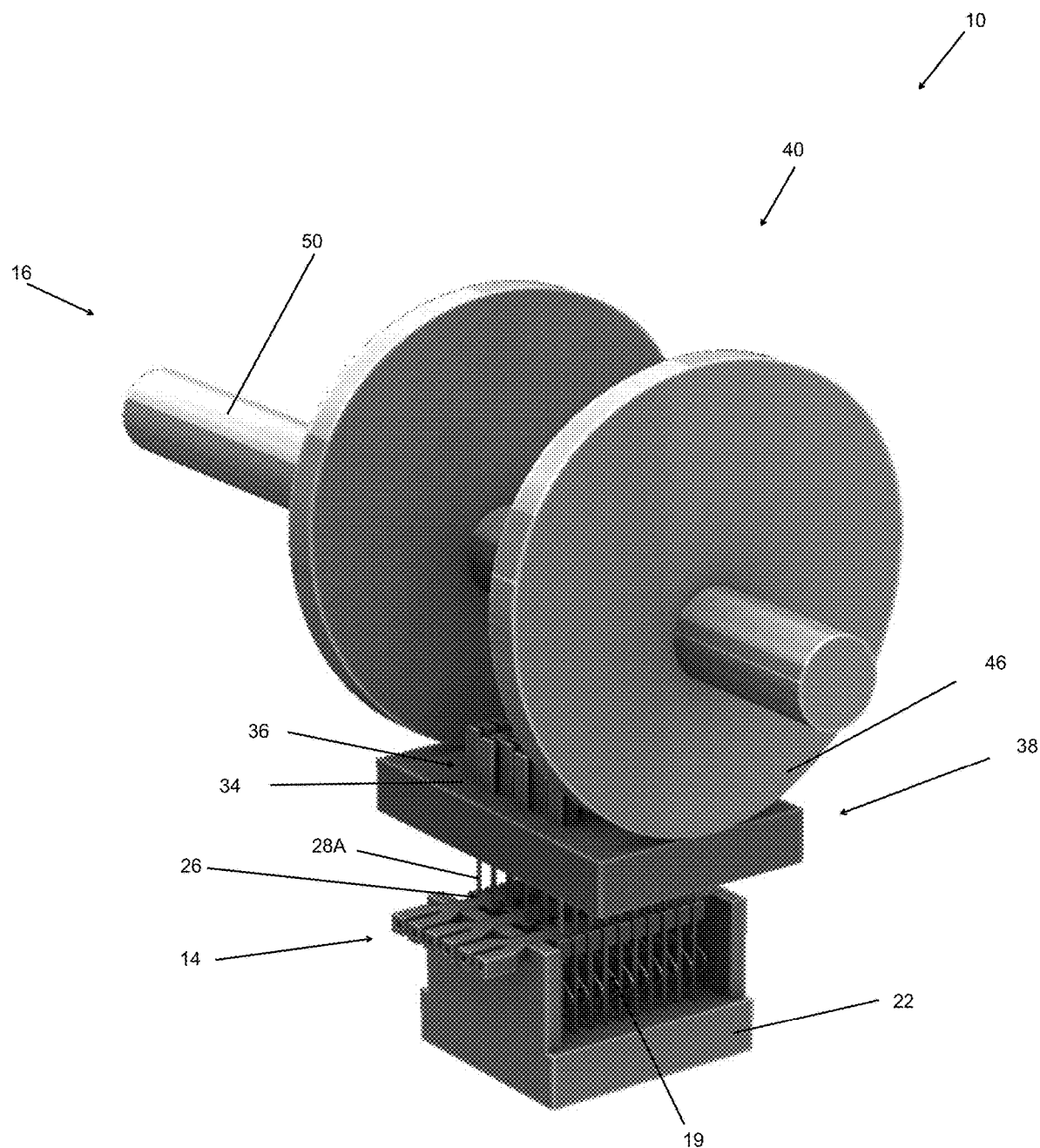
FIG. 2 is a perspective view of the ink deliver assembly of FIG. 1 shown connected to a drive mechanism in accordance with an illustrative embodiment of the raster injector disclosed herein.
Figure 3:
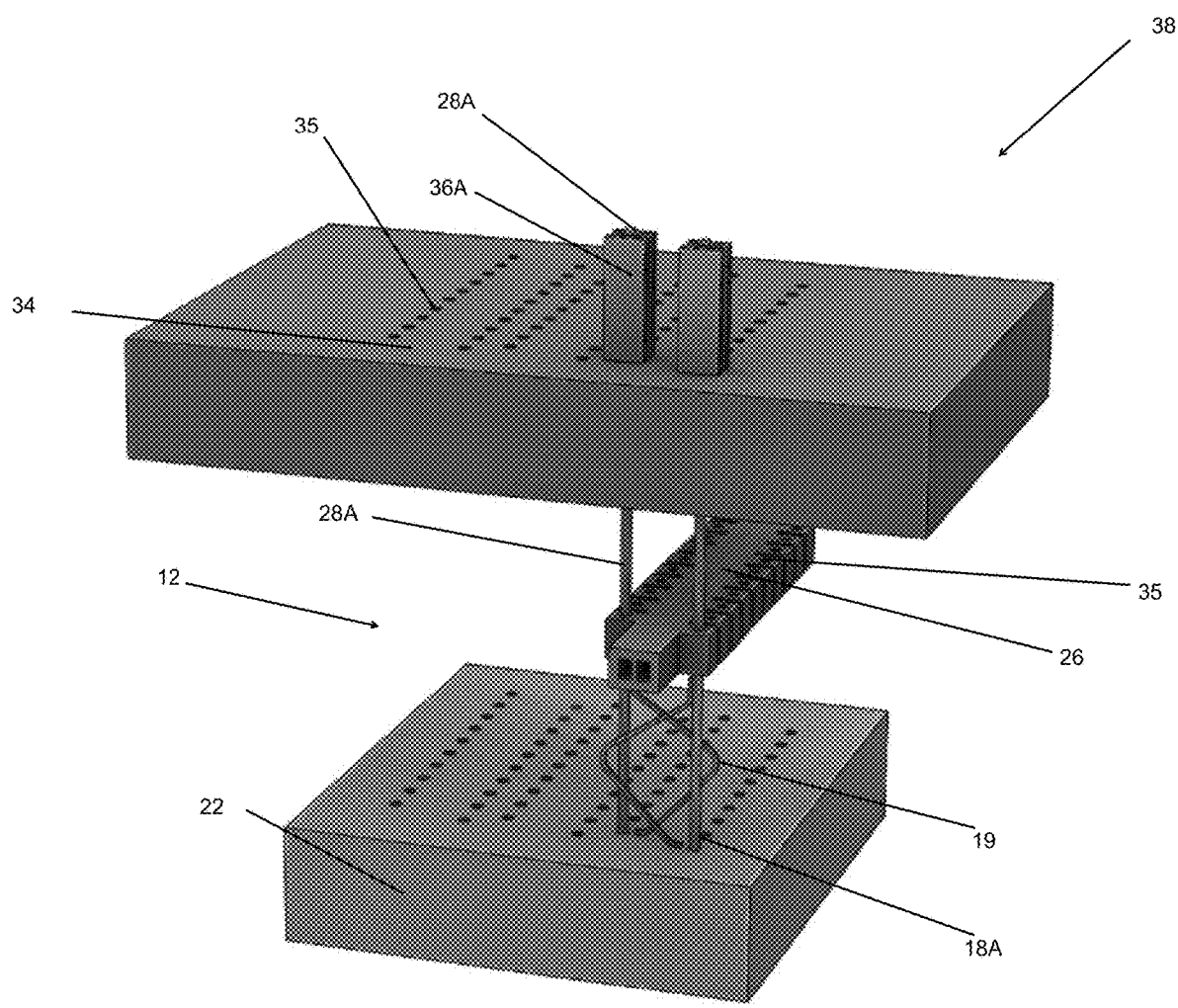
FIG. 3 is a perspective view of the ink deliver assembly of FIG. 1 shown with only two (2) needle units.
Figure 4:
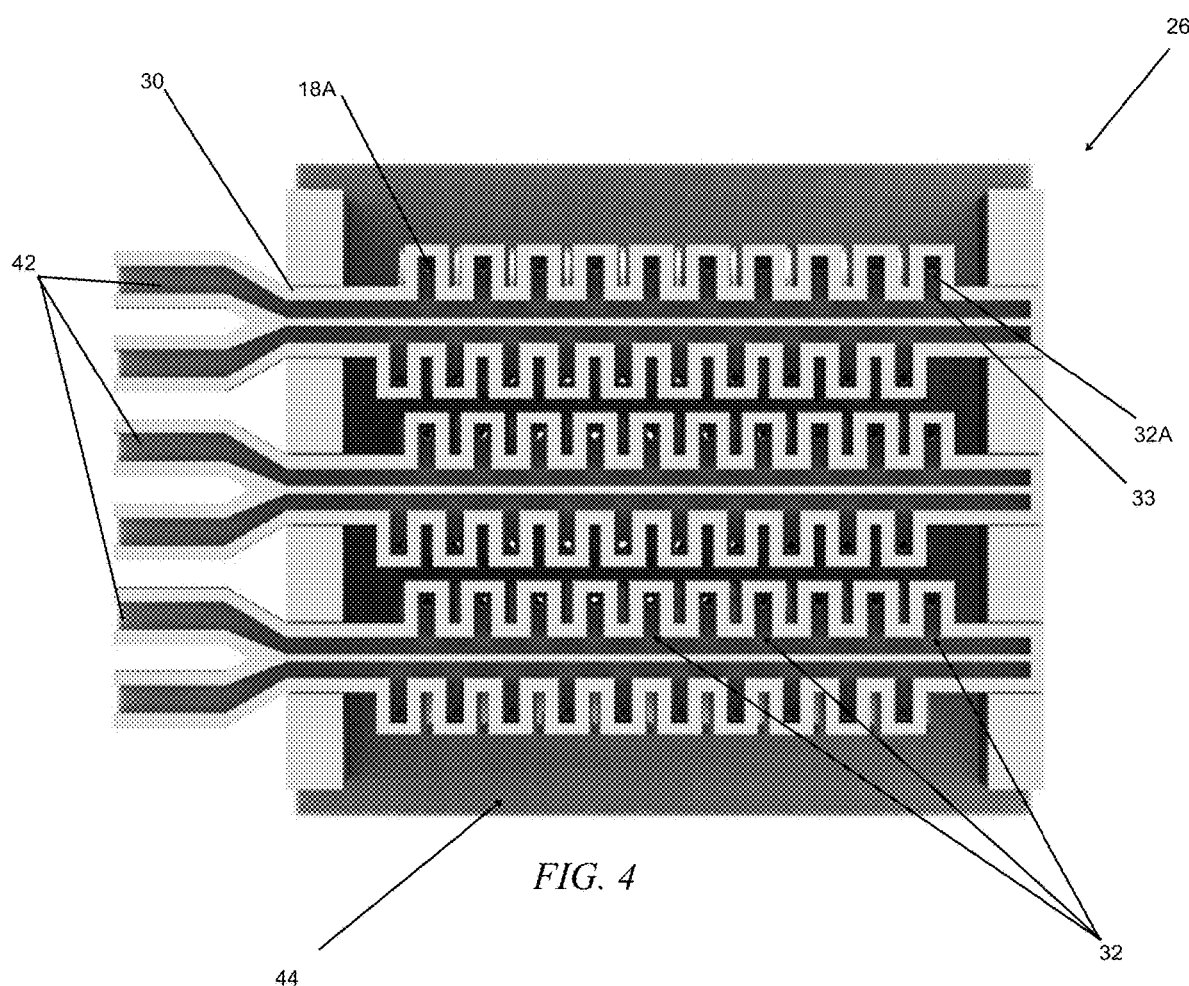
FIG. 4 is an in-plane cutaway view of an example of an ink distribution plate in accordance with an illustrative embodiment of the raster injector disclosed herein.
Figure 5:
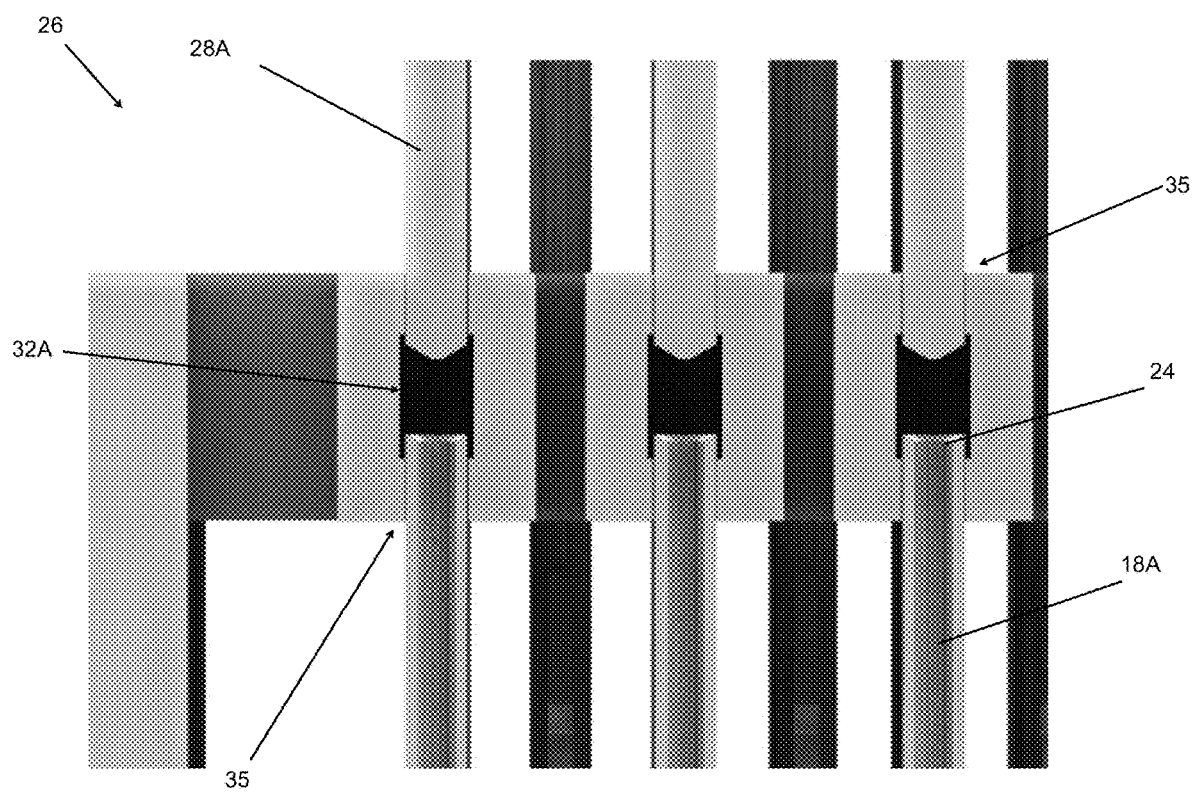
FIG. 5 is a cross-sectional view of an example of a disposable, interchangeable ink deliver assembly, an ink distribution plate, and an array of hollow needles in accordance with an illustrative embodiment of the raster injector disclosed herein.
Figure 6:
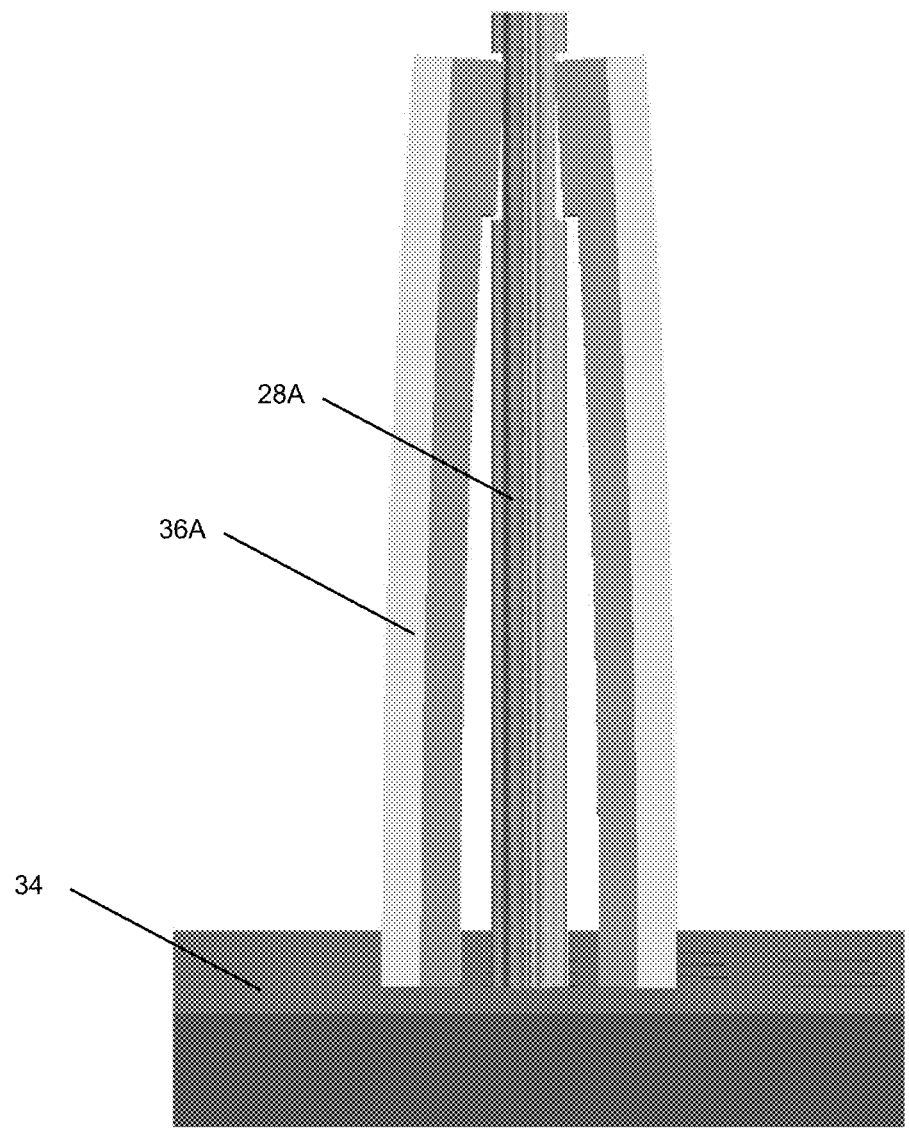
FIG. 6 is an elevation view of an example of an array of drive pins and an array of drive grippers in accordance with an illustrative embodiment of the raster injector disclosed herein.

The device and methods discussed herein are merely illustrative of specific manners in which to make and use this invention and are not to be interpreted as limiting in scope.

While the invention has been described with a certain degree of particularity, it is to be noted that many modifications may be made in the details of the construction and the arrangement of the elements and components of the devices and/or in the sequences and steps of the methods without departing from the scope of this disclosure. It is understood that the devices and methods are not limited to the embodiments set forth herein for purposes of exemplification.

The description of the invention is intended to be read in connection with the accompanying drawings, which are to be considered part of the entire written description of this invention. In the description, relative terms such as "front," "rear," "lower," "upper," "horizontal," "vertical," "above," "below," "up," "down," "top" and "bottom" as well as derivatives thereof (e.g., "horizontally," "downwardly," "upwardly" etc.) should be construed to refer to the orientation as then described or as shown in the drawings under discussion. These relative terms are for convenience of description and do not require that the machine be constructed or the method to be operated in a particular orientation. Terms, such as "connected," "connecting," "attached," "attaching," "join" and "joining" are used interchangeably and refer to one structure or surface being secured to another structure or surface or integrally fabricated in one piece.

Referring to the figures of the drawings, wherein like numerals of reference designate like elements throughout the several views, a raster injector of micropigmentation 10 includes a disposable, interchangeable ink delivery assembly 12, an ink reservoir assembly 14 and a non-disposable base assembly 16. As illustrated in the figures, the raster injector 10 may be constructed with sixty (60) needles 18, each having a diameter of about 0.25 mm. In this non-limiting example, in one operational pass, the raster injector 10 may produce ten (10) rows of dots with a spacing of 0.5 mm and six (6) colors in each row.

The disposable, interchangeable ink delivery assembly 14 includes an array of hollow needles 18 engaged with individual biasing mechanisms 19 and an array of drive pins 28. Each of the needles 18A of the array of needles 18 has a first terminal end 20 that may be sharpened and is engaged with a needle guide plate 22. The first terminal end 20 of the each of the needles 18A may either lie within or protrude from the needle guide plate 22 away from the rest of the raster injector 10. Each of the needles 18A also includes a second terminal end 24, which may be positioned within an ink distribution plate 26 when the needle 18A is retracted, or may be positioned in between the ink distribution plate 26 and the needle guide plate 22 when the needle 18A is extended. The array of needles 18 passes through the needle guide plate 22.

Each needle 18A is engaged with an individual biasing mechanism 19, for example a return spring, which causes each needle 18A to sit in the retracted position unless moved away from such position by drive pins 28A. The needles 18A contain ink (not shown) and follow an individually selectable, intermittent, reciprocating motion. The ink is periodically allowed to enter from the second terminal end 24 of the needle 18A, and the ink is periodically allowed to exit from the exposed, possibly sharpened end 20 of the needle 18A outside the raster injection 10. This periodic outflow of ink creates a mark or dot just below the surface of a substrate, which may be human skin or any other material into which the needles 18A can pierce. The dots created in this manner may be located in a known position, by virtue of the structure and control of the rest of the raster injection 10, and may form an image when viewed all together.

The needle guide plate 22 includes a plurality of holes, slots, or other features which constrain the motion of the array of needles 18 to be only in an axial direction. The needle guide plate 22 constrains the axis each needle 18A to be in a known position relative to the base assembly 16.

The ink distribution plate 26 has one or more axial bores 30, which guide ink from the ink reservoir assembly 14 to an array of induction chambers 32 within the ink distribution plate 26. Each induction chamber 32A has an entryway 33 within the ink distribution plate 26 for ink and an aperture 35 that passes through the ink distribution plate 26 creating two additional openings to the chamber 32A. One of these openings is continually blocked by a drive pin 28A of the array of drive pins 28, and the other opening is periodically blocked by a needle 18A from the array of hollow needles 18 or the drive pin 28A of the array of drive pins 28. As such, the drive pins 28A, in the course of their reciprocating motion, move from a retracted position where a first end lies within the ink distribution plate 26, to an extended position where the first end passes completely through the ink distribution plate 26. When a drive pin 28A is extended and passes all the way through the ink distribution plate 26, the drive pin 28A contacts and engages the needle 18A. When the drive pin 28A is retracted and the first end lies within the ink distribution plate 26, the drive pin 28A is no longer in contact with an associated needle 18A. This allows the ink within the ink induction chambers 32 to contact the end faces of both the drive pins 28 and the needles 18 periodically, when they are retracted.

The array of drive pins 28 pass through a drive pin guide plate 34 and an array of drive grippers 36 receiving intermittent reciprocal motion and transmitting that motion axially to the array of needles 18. One end of each drive pin 28A is situated to pass through or be gripped by one gripper 36A of array of drive grippers 36 and the other end of each drive pin 28A is situated to pass into or through one of the axial bores 30 of the ink distribution plate 26.

The drive pin guide plate 34, which may be integral to a drive plate 38 and/or the array of drive grippers 36, has a number of bores 39 each of which contain one drive pin 28A from the array of drive pins 28A and constrain the drive pins 28 to only move relative to the drive pin guide plate 34 along their axes. The drive pin guide plate 34 also aligns each drive pin 28A with its associated gripper 36A in the array of drive grippers 36. The drive pin guide plate 34 may also have other alignment features to constrain the possible motion relative to the other parts of the raster injector 10. By way of example, the drive plate 38 and the drive pin guide plate 34 may be constructed as a single integrated circuit board, with boreholes for the array of drive pins 28 and solder pads for the array of drive grippers 36.

The drive grippers 36 may be attached to or be integral with the drive plate 38 and/or the drive pin guide plate 34, and all move in unison. Each drive gripper 36A also provides a gripping action which is individually controlled by a multi-channel input from a control connection for the array of drive grippers 36. The gripping action of each single drive gripper 36A acts on a single drive pin 28A, and in this way, the reciprocating motion of the drive plate 38 may be selectively transmitted to each of the drive pins 28A.

The drive plate 38 receives forces and motion from a drive mechanism 40 of the base assembly 16, and transmits that motion to the array of drive grippers 36. The drive plate 38 may also have features to ensure proper alignment with the other parts of the ink delivery assembly 12, and may be combined with the array of drive grippers 36 and/or the drive pin guide plate 34 as a single part.

Referring now to the ink reservoir assembly 14, the raster injector 10 may utilize more than one type or color of ink, each of which need to be stored separately from each other and from the outside environment. One or more ink reservoirs 42 or any other part in the ink reservoir assembly 14 may include quick-disconnect functionality, long-term storage protection, shipping robustness, external indexing or labeling, automatic or manual identification functionality, and/or handling features.

During operation, the ink must flow from the ink reservoir assembly 14 to the ink delivery assembly through a nozzle assembly or other detachable passageway, which may contain check valves or other flow management devices or actuators. The raster injector 10 may also include mechanical alignment features, mechanical attachment features, and/or seals for ink, air, or other fluids. There will be pressure changes in the ink bores 30 and ink reservoirs 42 in conjunction with the flow of ink through the raster injector 10. An ink pressure management system 44 controls the flow of ink by relieving vacuum pressure in the ink reservoirs 42, creating positive pressure in the ink reservoirs 42, and/or controlling ink valves or other ink control actuators that may be part of the ink delivery assembly 12 and/or the ink reservoir assembly 14.

Referring now to the base assembly 16 of the raster injector 10, the raster injector 10 is coupled to a motion platform 46, capable of moving or positioning the raster injector 10 in one or more directions. The base assembly 16 may provide a single mounting point for the raster injector, or may be partially or fully integrated into the motion platform 46. A drive mechanism 40 takes the energy delivered by a drive power connection 50 and converts it into a reciprocating, forced, relative motion between the base assembly 16 and the drive plate 38 of the ink delivery assembly 12. This reciprocating motion pattern may contain high frequency or fast motions which are faster than those that the motion platform 46 can produce. The drive power connection 50 allows the base assembly 16 to obtain a controllable flow of energy, whether electrical, pneumatic, hydraulic, mechanical, or otherwise, which may be used to do mechanical work.

The ink delivery assembly 12 and the ink reservoir assembly 14 are positioned and held relative to each other and relative to the base assembly 16 to provide a connection for the ink to travel between those parts, to provide any necessary seals, and to cause the ink deliver assembly to follow the movements of the motion platform 46. These attachment and alignment features may optionally provide quick-disconnect functionality for the ink delivery assembly 12 and the ink reservoir assembly 14.

The array of drive grippers 36 requires a multi-channel control input, whether electrical, pneumatic, hydraulic, mechanical or of any other nature. The control input comes from the motion platform 46, such that the motion of the needles 18 may be synchronized with the motion of the rest of the raster injector 10.

Whereas, the devices and methods have been described in relation to the drawings and claims, it should be understood that other and further modifications, apart from those shown or suggested herein, may be made within the scope of the invention.

What is claimed is:

1. A raster injector assembly for micropigmentation, said assembly comprising:
    a disposable, interchangeable ink delivery assembly having an array of needles;
    an ink reservoir assembly configured to contain a plurality of inks, said ink reservoir assembly in fluid communication with said ink delivery assembly;
    a non-disposable base assembly connected to said ink delivery assembly and said ink reservoir assembly;
    a drive pin guide plate and an array of drive pins, wherein said drive pin guide plate constrains motion of said drive pins in an axial direction.

2. The assembly of claim 1 further comprising biasing mechanisms engaged with said array of needles.

3. The assembly of claim 2 wherein said biasing mechanisms are return springs.

4. The assembly of claim 1 wherein said ink delivery assembly further comprises a needle guide plate having axial bores that constrain motion of said needles in an axial direction.

5. The assembly of claim 1 wherein said ink delivery assembly further comprises an ink distribution plate having one or more axial bore passageways and an array of induction chambers.

6. The assembly of claim 1 wherein said ink delivery assembly further comprises an array of drive grippers engaged with a drive plate and/or said drive pin guide plate.

7. The assembly of claim 6 wherein each of said drive grippers is respectively engaged with said drive pin.

8. The assembly of claim 1 wherein said ink reservoir assembly further comprises a plurality of ink reservoirs respectively containing said inks.

9. The assembly of claim 1 wherein said ink reservoir assembly further comprises an ink pressure management system for controlling the flow of ink through the raster injector assembly.

10. The assembly of claim 1 wherein said base assembly further comprises a motion platform configured to move the raster injector assembly in one or more directions.

11. The assembly of claim 10 wherein said base assembly further comprises a drive mechanism for providing a reciprocating, forced, relative motion between the base assembly and a drive plate of said raster injector assembly.

* * * * *